United States Patent [19]
Soll et al.

[11] Patent Number: 5,482,942
[45] Date of Patent: Jan. 9, 1996

[54] (3,4-DIOXOCYCLOBUTEN-1-YL)CHROMENE, INDENE, AND DIHYDRONAPHTHALENONE DERIVATIVES AS SMOOTH MUSCLE RELAXANTS

[75] Inventors: Richard M. Soll, Lawrenceville, N.J.; Paul J. Dollings, Newtown, Pa.

[73] Assignee: American Home Products Corporation, Madison, N.J.

[21] Appl. No.: 267,691

[22] Filed: Jun. 28, 1994

[51] Int. Cl.⁶ .................. A61K 31/495; A61K 31/415; A61K 31/35; C07D 241/02; C07D 211/82; C07D 407/02; C07D 311/74; C07C 229/40

[52] U.S. Cl. .......... 514/254; 514/255; 514/256; 514/259; 514/266; 514/311; 514/314; 514/336; 514/337; 514/357; 514/375; 514/394; 514/406; 514/414; 514/415; 514/422; 514/427; 514/438; 514/443; 514/444; 514/456; 514/457; 514/461; 514/469; 514/510; 514/522; 514/524; 514/562; 514/563; 514/564; 514/567; 514/603; 514/616; 514/617; 514/618; 514/647; 544/283; 544/333; 544/335; 544/336; 544/405; 544/410; 560/6; 560/12; 560/13; 560/18; 560/19; 560/21; 560/22; 560/23; 560/45; 560/47; 560/48; 546/167; 546/173; 546/269; 546/329; 546/330; 546/332; 546/346; 549/49; 549/58; 549/60; 549/74; 549/75; 549/76; 549/77; 549/398; 549/404; 549/405; 549/406; 549/407; 549/408; 549/409; 549/410; 549/469; 549/471; 549/472; 549/473; 549/491; 549/496; 562/427; 562/433; 562/435; 562/443; 562/444; 562/448; 562/449; 562/450; 562/452; 562/455; 562/456; 562/457; 562/458; 548/217; 548/224; 548/300.1; 548/304.4; 548/305.1; 548/309.7; 548/364.4; 548/373.1; 548/454; 548/464; 548/469; 548/511; 548/516; 548/517; 548/525; 548/560; 548/563; 558/412; 564/80; 564/82; 564/83; 564/85; 564/86; 564/87; 564/154; 564/155; 564/156; 564/157; 564/162; 564/163; 564/166; 564/167; 564/307; 564/308

[58] Field of Search .................. 514/254, 255, 514/256, 259, 311, 314, 336, 357, 375, 394, 406, 414, 415, 422, 427, 438, 443, 444, 456, 457, 461, 469, 266, 337, 510, 522, 524, 562, 563, 564, 567, 603, 616, 617, 618, 647; 544/333, 335, 283, 405, 410, 336; 546/167, 173, 269, 329, 330, 332, 346; 558/412; 560/6, 12, 13, 18, 19, 21, 22, 23, 45, 47, 48; 562/427, 433, 435, 443, 444, 448, 449, 450, 452, 455, 456, 457, 458; 564/80, 82, 83, 85, 86, 87, 154, 155, 156, 157, 162, 163, 166, 167, 307, 308; 548/300.1, 224; 549/406, 471

[56] References Cited

U.S. PATENT DOCUMENTS 5,006,550  4/1991  Chandraratna ............ 514/456
5,071,871  12/1991  Blarer et al. ............ 514/456
5,134,159  7/1992  Chandraratna ............ 514/456
5,141,939  8/1992  Weissmüller et al. ........ 514/253
5,143,924  9/1992  Gerècke et al. ........... 514/337
5,210,234  5/1993  Evans et al. ............. 549/398
5,227,392  7/1993  Frickel et al. ........... 514/363
5,227,499  7/1993  McGowan et al. ........... 549/404

(List continued on next page.)

FOREIGN PATENT DOCUMENTS 0376524  7/1990  European Pat. Off. ...... C07D 311/68
0426379  5/1991  European Pat. Off. ...... C07D 311/68

OTHER PUBLICATIONS

Liebeskind and Fengl, J. Org. Chem. 55, 5359–5364 (1990).

Primary Examiner—Kimberly J. Kestler
Attorney, Agent, or Firm—R. F. Boswell, Jr.

[57] ABSTRACT

This invention relates to novel 4-3,4-dioxocyclobuten-1-yl)chromenes and dihydronaphthalenones and 3-3,4-dioxocyclobuten-1-yl)indenes and salts thereof having smooth muscle relaxing activity, to their use in the treatment of hypertension as well as for treatment of peripheral vascular disease, congestive heart failure, disorders involving excessive smooth muscle contraction of the urinary tract such as incontinence or of the gastrointestinal tract such as irritable bowel syndrome, asthma, and hair loss and to pharmaceutical compositions containing an invention compound. The present invention discloses compounds represented by the formula (I):

wherein:

$R_1$ and $R_2$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{1-6}$ alkoxycarbonyl, nitro, cyano, halogen, $C_{1-6}$ alkylsulfonamido, $C_{1-6}$ perfluoroalkylsulfonamido, amino, $C_{1-6}$ acylamino, $C_{1-6}$ perfluoroacylamino, mono or di-$C_{1-12}$ alkylamino, $C_{1-6}$ alkylsulfonyl, $C_{6-10}$ arylsulfonyl, carboxyl, $C_{1-12}$ mono or di-alkylaminocarbonyl, or hydrogen;

a and b together form an —O— linkage, C=O, or a direct bond:

$R_3$ and $R_4$, independent from each other, are H or $C_{1-6}$ alkyl, optionally substituted by fluorine;

$R_5$ is amino or $C_{1-12}$ mono alkylamine;

$R_6$ is H, $C_{1-6}$ perfluoroalkyl, $C_{1-6}$ alkyl, $C_{6-10}$ aryl, or mono or bicyclic heteroaryl containing 1–3 heteroatoms selected from N, O, or S.

5 Claims, No Drawings

U.S. PATENT DOCUMENTS

| | | | |
|---|---|---|---|
| 5,231,190 | 7/1993 | McGowan et al. | 549/13 |
| 5,232,944 | 8/1993 | Gerècke et al. | 514/456 |
| 5,236,935 | 8/1993 | Yoo et al. | 514/337 |
| 5,250,547 | 10/1993 | Lockhead et al. | 514/337 |
| 5,278,174 | 1/1994 | Erickson et al. | 514/320 |
| 5,298,512 | 3/1994 | Eggler et al. | 514/314 |
| 5,393,775 | 2/1995 | LeBaut et al. | 514/456 |
| 5,399,561 | 3/1995 | Chandrarantna | 514/252 |
| 5,412,117 | 5/1995 | Koga et al. | 549/404 |
| 5,414,006 | 5/1995 | Rendenbach-Mueller et al. | 514/363 |
| 5,426,229 | 6/1995 | Schaus et al. | 564/428 |

(3,4-DIOXOCYCLOBUTEN-1-YL)CHROMENE, INDENE, AND DIHYDRONAPHTHALENONE DERIVATIVES AS SMOOTH MUSCLE RELAXANTS

This invention relates to novel 4-(3,4-dioxocyclobuten-1-yl)chromenes, dihydronaphthalenones and 3-(3,4-dioxocyclobuten-1-yl)indenes or salts thereof having smooth muscle relaxing activity, to their use in the treatment of hypertension as well as for treatment of peripheral vascular disease, congestive heart failure, disorders involving excessive smooth muscle contraction of the urinary tract such as incontinence or of the gastrointestinal tract such as irritable bowel syndrome, asthma, and hair loss and to pharmaceutical compositions containing an invention compound.

6-Substituted-4-aminobenzopyrans useful in treating hypertension are disclosed in the published PCT patent applications WO 92/19611 and WO 92/20672, published European patent applications EP 0158923 and EP 0427606, and in U.S. Pat. Nos. 4,925,839, 4,908,378 and 4,616,021. 6-Substituted-4-amino tetrahydronaphthalene-1-ones having antihypertensive and bronchodilatory activity as disclosed in U.S. Pat. No. 5,208,246 and in the published European patent application EP 0413438. 5-Substituted-3-aminoindanes useful in treating hypertension and respiratory tract disorders are disclosed in published European patent applications EP 0413438 and EP 0426379 Antihypertensive 6-substituted-4-aminobenzopyrans, tetrahydronaphthalenes or tetrahydroquinolines are disclosed in the published European patent application EP 0376524. EP 0426379 discloses compounds having the formula where Y is N or $CR^1$, J is O or $NR^8$, and a and b together form an —O— or —$CH_2$— linkage or a bond used as bronchodilators, to lower blood pressure, and to treat respiratory tract disorders.

SUMMARY OF THE INVENTION

The present invention discloses compounds represented by the formula (I):

wherein:

$R_1$ and $R_2$, independent from each other, are selected from the following: $C_{1-6}$ perfluoroalkoxy, $C_{1-6}$ perfluoroalkyl, $C_{1-6}$ alky, $C_{1-6}$ alkoxy, hydroxyl, $C_{1-6}$ alkoxycarbonyl, nitro, cyano, halogen, $C_{1-6}$ alkylsulfonamido, $C_{1-6}$ perfluoroalkylsulfonamido, amino, $C_{1-6}$ acylamino, $C_{1-6}$ perfluoroacylamino, mono or di-$C_{1-12}$ alkylamino, $C_{1-6}$ alkylsulfonyl, $C_{6-10}$ arylsulfonyl, carboxyl, $C_{1-12}$ mono or di-alkylaminocarbonyl, or hydrogen;

a and b together form an —O— linkage, C=O, or a direct bond;

$R_3$ and $R_4$, independent from each other, are H or $C_{1-6}$ alkyl, optionally substituted by fluorine;

$R_5$ is amino or $C_{1-12}$ mono alkylamine;

$R_6$ is H, $C_{1-6}$ perfluoroalkyl, $C_{1-6}$ alkyl, $C_{6-10}$ aryl or mono or bicyclic heteroaryl containing 1–3 heteroatoms selected from N, O, or S; and pharmaceutically acceptable salts thereof.

The more preferred compounds of this invention are those of Formula 1 wherein $R_1$ and $R_2$, independent from each other, are trifluoromethoxy, methoxy, nitro, cyano, chloro, bromo, fluoro, trifluoromethyl, methanesulfonamido, mono or di-$C_{1-6}$-alkylamino, acetamido, trifluoroacetamido, trifluoromethylsulfonamido, or hydrogen;

a and b together form an —O— linkage or a direct bond;

$R_3$ and $R_4$ are methyl when a and b together form an —O— linkage;

$R_5$ is amino or $C_{1-12}$ mono alkylamine; and $R_6$ is $C_{1-6}$ alkyl or H.

The most preferred compounds of this invention are those of Formula 1 wherein:

$R_1$ is CN;

$R_2$ is H;

a and b together form an —O— linkage;

$R_3$ and $R_4$ are methyl;

$R_5$ is amino or methylamino; and $R_6$ is H.

The term "mono or bicyclic heteroaryl containing 1–3 heteroatoms selected from N, O, or S" means a heteroaryl moiety selected from the group consisting of quinoline, pyridine, indole, pyrrole, quinazoline, pyrazine, pyrimidine, thiophene, furan, benzofuran, benzimidazole, pyrazole, benzoxazole, and benzothiophene. The term alkyl, alone or in conjunction with another functional group such as carbonyl, sulfonamido, amino, carbamoyl, sulfonyl or carboxamido, encompasses straight and branched chain hydrocarbon radicals such as methyl, ethyl, propyl, isopropyl, butyl, tert-butyl, pentyl, neopentyl, hexyl, decyl, etc. within the limits set forth for the number of carbon atoms. The term perfluoroalkyl means an alkyl group as defined above wherein all of the hydrogen atoms are replaced by fluorine atoms. The term alkoxy alone or in conjunction with another functional group such as carbonyl means an —O— alkyl group where alkyl is as defined above and a perfluoroalkoxy group is an alkoxy group wherein the perfluoroalkyl group is as defined above. The term $C_{6-10}$ aryl means phenyl or naphthyl optionally substituted by halogen, cyano, nitro, $C_{1-6}$ alkyl, $C_{1-6}$ alkoxy, or $C_{3-6}$ cycloalkyl and may be used in conjunction with a functional group such as amino, sulfonyl, or oxy. The term $C_{1-6}$ acyl means a radical derived from a carboxylic acid of from one to six carbon atoms, such as formyl, acetyl, propionyl, butyryl, and the like and may be used in conjunction with another functional group or linking group such as amino or oxy. The term $C_{1-6}$ perfluoroacyl group is a $C_{1-6}$ acyl group as defined above wherein all of the hydrogens are replaced with fluorine atoms. The term $C_{1-6}$ alkyl optionally substituted by fluorine means an alkyl group wherein one or more hydrogens, up to the maximum number, are replaced by fluorine atoms.

The term "pharmaceutically acceptable salt" means an acid addition salt formed from a basic invention compound and a pharmaceutically acceptable acid including but not limited to such acids as acetic, hydrochloric, hydrobromic, sulfuric, phosphoric, maleic, fumaric, succinic, citric, malonic, tartaric, and methanesulfonic acids.

Unlike the compounds disclosed by EP 0426379, compounds of this invention have no intervening atom or group between the bicyclic benzo group and the cyclobutenediore group.

It should be recognized that the invention compounds and salts thereof may be isolated as solvates and hydrates and are considered pharmacologically equivalent to the invention compounds or salts thereof.

The compounds of formula (I) are smooth muscle relaxants. They are therefore useful in the treatment of hypertension as well as for treatment of peripheral vascular disease, congestive heart failure and disorders involving excessive smooth muscle contraction of the urinary tract (such as incontinence), or of the gastro-intestinal tract (such as irritable bowel syndrome), asthma, and hair loss.

The present invention accordingly provides a pharmaceutical composition which comprises a compound of this invention and a pharmaceutically acceptable carrier. The compositions are preferably adapted for oral administration. However, they may be adapted for other modes of administration, for example parenteral administration for patients suffering from heart failure.

The present invention further provides a compound of the invention for use as an active therapeutic substance. Compounds of formula (I) are of particular use in the treatment of hypertension and/or smooth muscle relaxation.

DETAILED DESCRIPTION OF THE INVENTION

The compounds of the present invention may be prepared by the methodology of Liebeskind et. al. (*J. Org. Chem.* 1990, 55, 5359). More particularly, the compounds of formula (II):

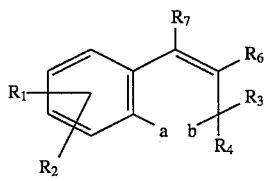

wherein $R_7$ is halogen or trifluromethanesulfonate along with $R_1$, $R_2$, $R_3$, $R_4$, $R_6$, a, and b as defined herein before or a group or atom convertible thereto are reacted with stannane of formula III

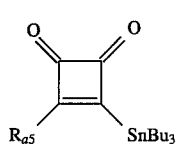

wherein $R_{a5}$ is typically O-alkyl to provide a compound of formula IV

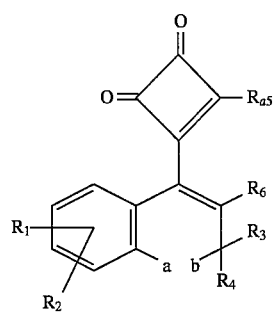

wherein $R_{a5}$ is O-alkyl. $Ra_5$ may then be convertible to $R_5$, for example when $R_{a5}$ is O-alkyl by treating with ammonia to give $R_5$ is $NH_2$.

The methods of preparation of Formula I compounds as given above are exemplified in the following specific examples. These examples are included for illustrative purposes only and are not intended to be limiting to this disclosure in any way. Still other methods of preparation may be apparent to those skilled in the art. Reactants and reagents used are either commercially available or can be prepared according to standard literature procedures.

EXAMPLE 1

4-(2-Isopropoxy-3,4-dioxo-cyclobut-1-enyl)-2,2-dimethyl-2H-chromene-6-carbonitrile.

The synthesis of 2,2-dimethyl-4-(O-triflate)-6-cyano-2H-1-benzopyran was accomplished in a manner to that reported by Yoo et. al. (EP 514942 A1) using 2,2-dimethyl-6-cyano-chromanone and trifluoromethanesulfonic acid anhydride. The preparation of tri-(2-furyl)phosphine was accomplished by the procedure of Allen et. al. (*J. Chem. Soc.* (*Perk. II*), 1972, 63). The preparation of 3-(1-methylethoxy)-4-(tri-n-butylstannyl)-3-cyclobutene-1,2-dione was performed by the procedure of Liebeskind et. al. (*J. Org. Chem.* 55, 5359 (1990)). To a solution of 2,2-dimethyl-4-(O-triflate)-6-cyano-2H-1-benzopyran(559 mg; 1.68 mmol), 720 mg (1.68 mmol) of 3-(1-methylethoxy)-4-(tri-n-butylstannyl)-3-cyclobutene-1,2-dione, 38.9 mg (0.168 mmol) of tri-(2-furyl)phosphine, and 457 mg (3.36 mmol) of zinc chloride in N-methylpyrrolidinene was purged with nitrogen. To this was added 48.3 mg (0.084 mmol) of bis(dibenzylideneacetone)palladium. The reaction mixture was then stirred at ambient temperature for 30 min and then at 65° C. for 1 h. The reaction mixture was diluted with $Et_2O$ (75 mL), and sequentially washed with sat. aq. $NH_4Cl$ (3×), $H_2O$ (3×), brine (3×), and then 10% KF (3×). The organic phase was dried ($Na_2SO_4$) and concentrated to give 598 mg of material which was combined with an identical run using 255 mg of 2,2-dimethyl-4-(O-triflate)-6-cyano-2H-1-benzopyran.

Purification by flash chromatography (20% EtOAc-hexane) gave 552 mg (70% yield) of the title compound as a yellow solid, mp 169°–170° C.: $^1$H-NMR (DMSO-$d_6$; 400 MHz) δ7.85 (d, 1H), 7.70 (dd, 1H), 7.04 (d, 1H), 6.67 (s, 1H), 5.49 (septet, 1H), 1.48 (s, 6H), and 1.44 ppm (d, 6H); IR (KBr) 2220, 1780, 1750, 1615, and 1570 cm$^{-1}$; mass spectrum (EI), m/e 323.

Anal. Calcd. for $C_{19}H_{17}NO_4$: C, 70.58; H, 5.30; N, 4.33. Found: C, 70.59; H, 5.26; N, 4.22.

EXAMPLE 2

4-(2-Amino-3,4-dioxo-cyclobut-1-enyl)-2,2-dimethyl-2H-chromene-6-carbonitrile.

Ammonia gas was bubbled into a solution of 361 mg (1.12 mmol) of 4-(2-isopropoxy-3,4-dioxo-cyclobut-1-enyl)-2,2-dimethyl-2H-chromene-6-carbonitrile in acetonitrile (11 ml) for 30 min. The reaction mixture was stirred at ambient temperature for 16 h. The reaction mixture was quenched with $H_2O$ (50 mL) and was extracted into 20% THF-$CH_2Cl_2$. The combined organic extracts were dried over anhydrous $Na_2SO_4$ and then concentrated and recrystallized from acetone-petroleum ether to give 110 mg of the title compound (35% yield), mp>250° C., as an off white solid: $^1$H-NMR (DMSO-$d_6$; 400 MHz) δ9.18 (bs, 1H), 8.68 (bs, 1H), 7.79 (d, 1H), 7.67 (dd, 1H), 7.01 (d, 1H), 6.29 (s, 1H), and 1.47 ppm (s, 6H); IR (KBr) 3300, 3100, 1780, 1730, 1720, 1665, and 1610 $cm^{-1}$; mass spectrum (PBEI), m/e 281 (M+H), 280 ($M^+$), 252, and 209.

Anal. Calcd. for $C_{16}H_{12}N_2O_3$: C, 68.57; H, 4.32; N, 9.99. Found: C, 68.47; H, 4.25; N, 9.99.

EXAMPLE 3

2,2-Dimethyl-4-(2-methylamino-3,4-dioxo-cyclobut-1-enyl)-2H-chromene-6-carbonitrile.

To a solution of 437 mg (1.35 mmol) of 4-(2-isopropoxy-3,4-dioxo-cyclobut-1-enyl)-2,2-dimethyl-2H-chromene-6-carbonitrile in $CH_3CN$ 14 mL) was added dropwise 8.03M methylamine in EtOH. The reaction mixture was stirred at ambient temperature for 1 h. The reaction mixture was quenched with $H_2O$ (50 mL) and then was extracted into 20% THF-$CH_2Cl_2$. The combined organic extracts were dried ($Na_2SO_4$) and purified by flash chromatography (4% MeOH—$CHCl_3$) and crystallization from $CH_2Cl_2$-petroleum ether to give 210 mg (53% yield) of the title compound, mp 193°–194° C., as a white solid: $^1$H-NMR (DMSO-$d_6$; 400 MHz; major rotamer) δ8.7–8.8 (br q, 1H), 7.78 (d, 1H), 7.67 (dd, 1H), 7.01 (d, 1H), 6.22 (s, 1H), 3.25 (d, 3H), and 1.46 ppm (s, 3H); IR (KBr) 2220, 1775, 1735, 1620 $cm^{-1}$; mass spectrum ($DCI^+$), m/e 2.95.

Anal. Calcd. for $C_{17}H_{14}N_2O_3 \cdot 0.25\ H_2O$: C, 68.33; H, 4.89; N, 9.37. Found: C, 68.56; H, 4.75; N, 9.54.

PHARMACOLOGY

Bladder Smooth Muscle

Bladder smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The bladder is removed into warm (37° C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 ml tissue bath under an initial resting tension of 1.5 g. The strips are held in place by two surgical clips one of which is attached to fixed hook while the other is attached to an isometric force transducer. The preparations, which usually exhibit small spontaneous contractions, are allowed to recover for a period of 1 hour prior to a challenge with 0.1 uM carbachol. The carbachol is then washed out and the tissue allowed to relax to its resting level of activity. Following one further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last min of a 30 min challenge.

Isometric force developed by the bladder strips is measured using a concentration required to elicit 50% inhibition of pre-drug contractile activity ($IC_{50}$ concentration) is calculated from this concentration-response curve. This maximum percentage inhibition of contractile activity evoked by a test compound is also recorded for concentrations of test compound less than or equal to 30 uM.

Aortic Smooth Muscle

Aortic smooth muscle relaxing activity of the compounds of this invention was established in accordance with standard pharmaceutically accepted test procedures in representative compounds as follows:

Sprague-Dawley rats (150–200 g) are rendered unconscious by $CO_2$ asphyxiation and then euthanized by cervical dislocation. The thoracic aorta is removed into warm (37° C.) Krebs-Henseleit solution. The aorta is cleaned of fat and loose adventitia and cut into rings 3–4 mm in width. The rings are subsequently suspended between two stainless steel wire tissue holders in a 10 ml tissue bath. One wire tissue holder is attached to fixed hook while the other is attached to an isometric force transducer. Resting tension is set at 1.0 g. The tissues are allowed to recover for a period of 60 mins prior to beginning the experiment. The tissues are challenged with 25 mM KCl to elicit a contracture. The tissue are then washed repeatedly with fresh Krebs-Henseleit solution over a period of 30 mins and allowed to recover to baseline tension. 25 mM KCl is then introduced into the tissue bath to evoke a contracture that is allowed to stabilize for not less than 45 mins. Increasing concentrations of test compound or vehicle are then added to the tissue bath in a cumulative fashion.

Isometric force developed by the aortic rings is measured using force transducer and recorded on a polygraph. The percentage inhibition of contractile force evoked by each concentration of a given test compound is used to generate a concentration-response curve. The concentration required to elicit 50% inhibition of pre-drug contractile activity ($IC_{50}$ concentration) is calculated from this concentration-response curve. The maximum percentage inhibition of contractile activity evoked by a test compound is also recorded for concentrations of test compound less than or equal to 30 uM.

The results of the above pharmacological assays are shown in Table I below.

TABLE I

Inhibition of Contractions in Isolated Rat Bladder and Aortic Tissue

| Compound | $IC_{50}$ or (% Inhibition of Bladder Contraction at 30 μM) | $IC_{50}$ or (% Inhibition of Aorta Contraction at 30 μM) |
| --- | --- | --- |
| Example 2 | 0.39 ± 0.04 μM | 0.15 ± 0.02 μM |
| Example 3 | 4.1 ± 1.8 μM | 0.56 ± 0.04 μM |

Hence, the compounds of this invention have a pronounced effect on smooth muscle contractility and are useful in the treatment of hypertension, urinary incontinence, irritable bladder and bowel disease, asthma, stroke and similar disease states as mentioned above, which are amenable to treatment with compounds by administration, orally, parenterally, or by aspiration to a patient in need thereof.

PHARMACEUTICAL COMPOSITION

When the compounds of the invention are employed in the treatment of diseases or disorders associated with smooth muscle contractions, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may also be injected intravenously or parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be formulated into dry aerosol inhalation formulations.

The dosage requirements vary with the particular compositions employed, the route of administration, the severity of the symptoms presented and the particular subject being treated. Treatment will generally be initiated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times throughout the day.

What is claimed is:

1. A compound according to the formula below:

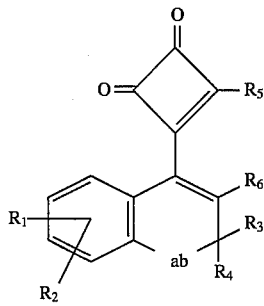

I wherein:

$R_1$ and $R_2$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{1-6}$ alkoxycarbonyl, nitro, cyano, halogen, $C_{1-6}$ alkylsulfonamido, $C_{1-6}$ perfluoroalkylsulfonamido, amino, $C_{1-6}$ acylamino, $C_{1-6}$ perfluoroacylamino, mono or di-$C_{1-12}$ alkylamino, $C_{1-6}$ alkylsulfonyl, $C_{6-10}$ arylsulfonyl, carboxyl, $C_{1-12}$ mono or di-alkylaminocarbonyl, or hydrogen;

a and b together form an —O— linkage, C═O, or a direct bond;

$R_3$ and $R_4$, independent from each other, are H or $C_{1-6}$ alkyl, optionally substituted by fluorine;

$R_5$ is amino or $C_{1-12}$ mono alkylamine;

$R_6$ is H, $C_{1-6}$ perfluoroalkyl, $C_{1-6}$ alkyl, $C_{6-10}$ aryl, or mono or bicyclic heteroaryl containing 1–3 heteroatoms selected from N, O, or S; or a pharmaceutically acceptable salt thereof.

2. A compound according to claim 1 wherein $R_1$ and $R_2$, independent from each other, are trifluoromethoxy, methoxy, nitro, cyano, chloro, bromo, fluoro, trifluoromethyl, methanesulfonamido, mono or di-$C_{1-6}$-alkylamino, acetamido, trifluoroacetamido, trifluoromethylsulfonamido, or hydrogen;

a and b together form an —O— linkage or a direct bond;

$R_3$ and $R_4$ are methyl when a and b form an —O— linkage;

$R_5$ is amino or $C_{1-12}$ mono alkylamine; and $R_6$ is $C_{1-6}$ alkyl or H.

3. A compound according to claim 1 wherein:

$R_1$ is CN;

$R_2$ is H;

a and b together form an —O— linkage;

$R_3$ and $R_4$ are methyl;

$R_5$ is amino or methylamino; and $R_6$ is H.

4. A compound according to claim one which is selected from:

4-(2-isopropoxy-3,4-dioxo-cyclobut-1-enyl)-2,2-dimethyl-2H-chromene-6-carbonitrile.

4-(2-amino-3,4-dioxo-cyclobut-1-enyl)-2,2-dimethyl-2H-chromene-6-carbonitrile, or 2,2-dimethyl-4-(2-methylamino-3,4-dioxo-cyclobut-1-enyl)-2H-chromene-6-carbonitrile.

5. A pharmaceutical composition for the treatment of diseases and disorders attributed to smooth muscle contraction which comprises a pharmaceutically acceptable carrier and a therapeutically effective amount of a compound of the formula:

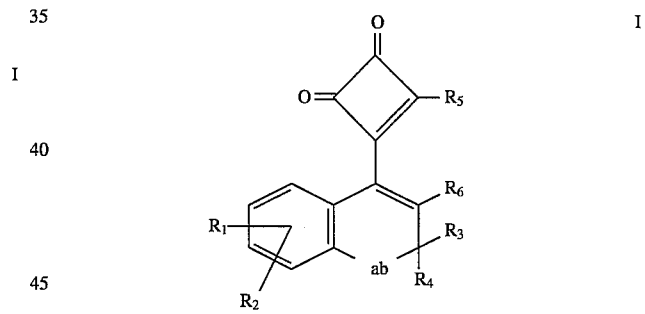

I wherein:

$R_1$ and $R_2$, independent from each other, are selected from the following: $C_{1-6}$ perfluoroalkoxy, $C_{1-6}$ perfluoroalkyl, $C_{1-6}$ alkyl, $C_{1-6}$ alkoxy, hydroxyl, $C_{1-6}$ alkoxycarbonyl, nitro, cyano, halogen, $C_{1-6}$ alkylsulfonamido, $C_{1-6}$ perfluoroalkylsulfonamido, amino, $C_{1-6}$ acylamino, $C_{1-6}$ perfluoroacylamino, mono or di-$C_{1-12}$ alkylamino, $C_{1-6}$ alkylsulfonyl, $C_{6-10}$ arylsulfonyl, carboxyl, $C_{1-12}$ mono or di-alkylaminocarbonyl, or hydrogen;

a and b together form an —O— linkage, C═O, or a direct bond;

$R_3$ and $R_4$, independent from each other, are H or $C_{1-6}$ alkyl, optionally substituted by fluorine;

$R_5$ is amino or $C_{1-12}$ mono alkylamine;

$R_6$ is H, $C_{1-6}$ perfluoroalkyl, $C_{1-6}$ alkyl, $C_{6-10}$ aryl, or mono or bicyclic heteroaryl containing 1–3 heteroatoms selected from N, O, or S; or a pharmaceutically acceptable salt thereof.

* * * * *